(12) United States Patent
Liu et al.

(10) Patent No.: US 10,856,995 B2
(45) Date of Patent: Dec. 8, 2020

(54) ARTIFICIAL VERTEBRAL FIXING SYSTEM

(71) Applicant: Beijing AK Medical Co., Ltd, Beijing (CN)

(72) Inventors: Zhongjun Liu, Beijing (CN); Caimei Wang, Beijing (CN)

(73) Assignee: BEIJING AK MEDICAL CO., LTD (CN)

( * ) Notice: Subject to any disclaimer, the term of this patent is extended or adjusted under 35 U.S.C. 154(b) by 0 days.

(21) Appl. No.: 16/324,381

(22) PCT Filed: Aug. 10, 2016

(86) PCT No.: PCT/CN2016/094396
§ 371 (c)(1),
(2) Date: Feb. 8, 2019

(87) PCT Pub. No.: WO2018/027676
PCT Pub. Date: Feb. 15, 2018

(65) Prior Publication Data
US 2019/0192306 A1 Jun. 27, 2019

(51) Int. Cl.
*A61B 17/70* (2006.01)
*A61F 2/44* (2006.01)
(Continued)

(52) U.S. Cl.
CPC ............... *A61F 2/44* (2013.01); *A61B 17/70* (2013.01); *A61B 17/7002* (2013.01); *A61F 2/28* (2013.01);
(Continued)

(58) Field of Classification Search
CPC ............ A61B 17/7044; A61B 17/7049; A61B 17/8695; A61B 17/8052; A61B 17/8057;
(Continued)

(56) References Cited

U.S. PATENT DOCUMENTS 2,448,351 A * 8/1948 Brush .................. F16B 37/043
411/80.5
5,616,052 A * 4/1997 Pan ...................... F16B 37/043
411/182
(Continued)

FOREIGN PATENT DOCUMENTS

CN 2584140 Y 11/2003
CN 2642266 Y 9/2004
(Continued)

OTHER PUBLICATIONS

PCT, "International Search Report and Written Opinion", Application No. PCT/CN2016/094396, dated May 15, 2017, 13 pages.
(Continued)

*Primary Examiner* — Jan Christopher L Merene
(74) *Attorney, Agent, or Firm* — Dorsey & Whitney LLP

(57) ABSTRACT

Provided is an artificial vertebral fixing system. The artificial vertebral fixing system includes: an artificial vertebral main body, arranged between adjacent human physiological vertebrae; two longitudinal connecting rods, respectively arranged at two sides of spinous processes of the human physiological vertebrae; a transverse connecting screw, connected between the artificial vertebral main body and each of the longitudinal connecting rods; and a connecting portion, connected to the artificial vertebral main body; when the connecting portion is provided with a self-tapping through hole, the transverse connecting screw is formed into thread structure by self-tapping when being screwed to the self-tapping through hole; and when the connecting portion is provided with a threaded hole, the transverse connecting screw is matched with the threaded hole. According to the technical scheme of the disclosure, the problem that the artificial vertebra has a poor stability in the related technology is effectively solved.

9 Claims, 7 Drawing Sheets

(51) Int. Cl.
*A61F 2/28* (2006.01)
*A61F 2/30* (2006.01)
(52) U.S. Cl.
CPC ...... *A61F 2/30749* (2013.01); *A61F 2002/30433* (2013.01); *A61F 2002/30578* (2013.01)
(58) Field of Classification Search
CPC ..... F16B 37/043; F16B 13/04; F16B 13/0833; Y10T 403/4662; Y10T 403/4665; Y10T 403/4668
USPC ........................................................ 411/182
See application file for complete search history.

(56) References Cited

U.S. PATENT DOCUMENTS

| | | | | |
|---|---|---|---|---|
| 6,540,746 | B1* | 4/2003 | Buhler | A61B 17/8047 606/282 |
| 8,506,605 | B2* | 8/2013 | Bickley | A61B 17/686 606/280 |
| 2004/0073218 | A1* | 4/2004 | Dahners | A61B 17/8057 606/287 |
| 2004/0254579 | A1* | 12/2004 | Buhren | A61B 17/8033 606/71 |
| 2005/0043736 | A1* | 2/2005 | Mathieu | A61B 17/8047 606/288 |
| 2006/0074421 | A1* | 4/2006 | Bickley | A61B 17/686 606/290 |
| 2006/0116678 | A1* | 6/2006 | Impellizzeri | A61B 17/8057 606/291 |
| 2008/0281361 | A1 | 11/2008 | Vittur et al. | |
| 2008/0281424 | A1 | 11/2008 | Parry et al. | |
| 2010/0082070 | A1* | 4/2010 | Diez | A61B 17/80 606/286 |
| 2013/0289628 | A1* | 10/2013 | Fritzinger | A61B 17/8047 606/290 |
| 2016/0058575 | A1 | 3/2016 | Sutterlin et al. | |
| 2017/0119537 | A1* | 5/2017 | Tepper | A61B 17/7059 |

FOREIGN PATENT DOCUMENTS

| | | |
|---|---|---|
| CN | 201029926 Y | 3/2008 |
| CN | 203138656 U | 8/2013 |
| CN | 106308916 A | 1/2017 |
| EP | 1188424 A1 | 3/2002 |
| WO | 2014144379 A1 | 9/2014 |

OTHER PUBLICATIONS

European Patent Office, "European Search Report for App. No. 16912131.6", dated Feb. 24, 2020.

* cited by examiner

ARTIFICIAL VERTEBRAL FIXING SYSTEM

TECHNICAL FIELD

The disclosure relates to the field of orthopedic implants, and more particularly, to an artificial vertebral fixing system.

BACKGROUND

In the treatment of human spinal diseases, spinal tumors, tuberculosis and severe fractures often lead to damage to a vertebra and are likely to hurt a spinal nerve such that a vertebral excision must be applied. For a spine having the excised vertebra, there is a need to reconstruct its stability, and the emergence of an artificial vertebral replacement provides a relatively ideal method for the treatment of such diseases. Since it was first reported in the late 1950s that a vertebral tumor was excised and was replaced by the prosthesis, an artificial vertebra has been widely applied in clinic as a type of effective vertebral replacement.

However, in clinical applications and in a series of biomechanical tests, it shows that the conventional artificial vertebra has some problems to be solved in certain aspects. Particularly, the stability in respect of postoperative axial rotation is inadequate and the early bonding strength with upper and lower vertebrae is low such that it is easy for an implant to shift or even to drop out. To guarantee a bone mass of a bone grafting hole in a center, the design areas for upper and lower end plates of the artificial vertebra are reduced, the support force is inadequate and thus the artificial vertebra is trapped in the end plates of the upper and lower vertebrae to lose its ideal height finally.

To reduce the influence of the above problems, while implanting an artificial vertebral main body, people have to provide an anterior or posterior screw-plate or screw-rod fixing system additionally in hoping to improve the stability during an early period and a bone fusion period. In the related technology, the anterior or posterior screw-plate or screw-rod fixing system is often connected with the artificial vertebral main body by transverse screws. The transverse screws and the artificial vertebral main body is connected by matching between outer screw threads and threaded holes. It is found in the clinic and in the biomechanical tests that the matching between the outer screw threads and the threaded holes is not stable enough after a period of time of use and the condition that the screw threads are dropped out occurs easily; and consequently, the artificial vertebral main body is shifted or even is dropped out.

SUMMARY

Some embodiments of the disclosure provide an artificial vertebral fixing system, so as to solve the problem that the artificial vertebra has a poor stability in the related technology.

To this end, an embodiment of the disclosure, there is provided an artificial vertebral fixing system, including: an artificial vertebral main body, arranged between adjacent human physiological vertebrae; two longitudinal connecting rods, respectively arranged at two sides of spinous processes of the human physiological vertebrae; a transverse connecting screw, connected between the artificial vertebral main body and each of the longitudinal connecting rods; and a connecting portion, connected to the artificial vertebral main body; the connecting portion is provided with a self-tapping through hole or a threaded hole; when the connecting portion is provided with the self-tapping through hole, the transverse connecting screw is formed into thread structure by self-tapping when being screwed to the self-tapping through hole; and when the connecting portion is provided with the threaded hole, the transverse connecting screw is matched with the threaded hole.

In an exemplary embodiment, the artificial vertebral main body includes an earring structure; the connecting portion is penetrated into a connecting hole of the earring structure; the connecting portion includes a connecting portion main body and a rotation stopping portion arranged on the connecting portion main body; the rotation stopping portions are abutted against and matched with a limiting portion of the artificial vertebral main body.

In an exemplary embodiment, the rotation stopping portion is arc block.

In an exemplary embodiment, the connecting portion further includes a locking mechanism; the connecting portion is limited in the connecting hole by the locking mechanism.

In an exemplary embodiment, the connecting portion main body is provided with a first end towards the longitudinal connecting rods and a second end far away from the longitudinal connecting rods; the rotation stopping portion is arranged at the first end of the connecting portion main body; the locking mechanism is arranged at the second end of the connecting portion main body.

In an exemplary embodiment, the locking mechanism includes a first fixture block and a second fixture block that are arranged oppositely; the first fixture block and the second fixture block are protruded from the connecting portion main body on a radial direction of the connecting portion main body; a deformation gap is formed between the first fixture block and the second fixture block.

In an exemplary embodiment, the locking mechanism further includes a transitional straight tube section; a first end of the transitional straight tube section is connected with the connecting portion main body; the first fixture block and the second fixture block are connected to the transitional straight tube section and are protruded from the transitional straight tube section on a radial direction of the transitional straight tube section; the transitional straight tube section is provided with a cutting groove communicating with the deformation gap.

In an exemplary embodiment, a circumferential outer surface of the connecting portion main body is of a conical shape; an outer diameter of the connecting portion main body is gradually reduced on a direction from the first end of the connecting portion main body to the second end of the connecting portion main body; the connecting hole of the earring structure is a conical hole matched with the connecting portion main body.

In an exemplary embodiment, a clamping step is arranged in the connecting hole of the earring structure; the locking mechanism is matched with the clamping steps.

In an exemplary embodiment, a longitudinal through hole is formed on the artificial vertebral main body.

In an exemplary embodiment, the artificial vertebral fixing system further includes fixing plates arranged on end portions of the artificial vertebral main body; the fixing plates are configured to connect with the human physiological vertebrae; a fixing hole is formed on each of the fixing plates.

In an exemplary embodiment, the artificial vertebral fixing system further includes pedicle screws: the longitudinal connecting rods and the human physiological vertebrae are connected via the pedicle screws.

In an exemplary embodiment, the transverse connecting screw is the same as each of the pedicle screws in structure.

In an exemplary embodiment, the artificial vertebral main body is obtained according to Computed Tomography (CT) data of a patient.

By applying the technical solution of the disclosure, the artificial vertebral fixing system includes the artificial vertebral main body, the two longitudinal connecting rods, the transverse connecting screw and the connecting portion. Herein, the artificial vertebral main body is arranged between the adjacent human physiological vertebrae and the two longitudinal connecting rods are respectively arranged at the two sides of the spinous processes of the human vertebrae. The artificial vertebral main body is connected to the longitudinal connecting rods via the transverse connecting screw. In the disclosure, the connecting portion is connected to the artificial vertebral main body, and the connecting portion is provided with the self-tapping through hole or the threaded hole. When the connecting portion is provided with the self-tapping through hole, the transverse connecting screw is formed into the thread structure by self-tapping when being screwed to the self-tapping through hole; and when the connecting portion is provided with the threaded hole, the transverse connecting screw is matched with the threaded hole. In this way, the transverse connecting screw can be closely matched with the screw structure formed by self-tapping or the threaded hole, and the connection is stable; as a result, the transverse connecting screw and the connecting portion are connected stably and the condition that screw thread is dropped out does not occur. Therefore, the artificial vertebral fixing system of the disclosure has a good stability, and the shift phenomenon in the related technology does not occur.

BRIEF DESCRIPTION OF THE DRAWINGS

The accompanying drawings are described here to provide further understanding of the disclosure, and form a part of the disclosure. The schematic embodiments and description of the disclosure are adopted to explain the disclosure, and do not form improper limits to the disclosure. In the drawings.

Herein, the above accompanying drawings include the following labels:

1, a human physiological vertebra; 2, a spinal cord; 10, an artificial vertebral main body; 11, an earring structure; 111, a connecting hole; 112, a clamping step; 12, a limiting portion; 13, a longitudinal through hole; 14, a fixing plate; 20, a longitudinal connecting rod; 30, a transverse connecting screw; 40, a connecting portion; 41, a self-tapping through hole; 42, a connecting portion main body; 43, a rotation stopping portion; 50, a locking mechanism; 51, a first fixture block; 52, a second fixture block; 53, a transitional straight tube section; 60, a pedicle screw.

DETAILED DESCRIPTION OF THE EMBODIMENTS

It is to be noted that the embodiments of the disclosure and the characteristics of the embodiments may be combined with each other if there is no conflict. The disclosure will be described below with reference to the drawings and embodiments in detail.

Figure 1:
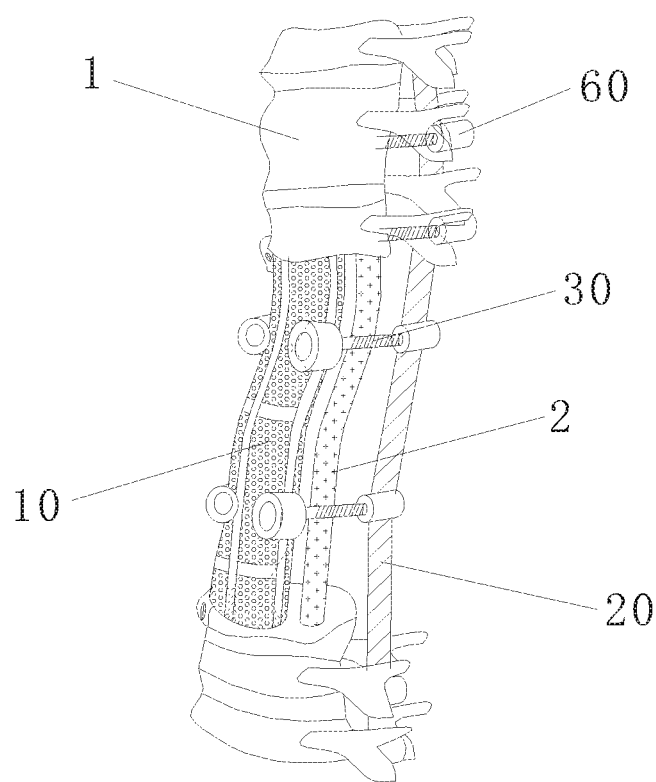
FIG. 1 depicts a structure diagram according to an embodiment of an artificial vertebral fixing system of the disclosure.

FIG. 1 depicts a structure diagram according to an embodiment of an artificial vertebral fixing system of the disclosure. As shown in FIG. 1, the artificial vertebral fixing system in the embodiment includes: an artificial vertebral main body 10, two longitudinal connecting rods 20, transverse connecting screws 30 and connecting portions 40. Herein, the artificial vertebral main body 10 is arranged between adjacent human physiological vertebrae 1, and the two longitudinal connecting rods 20 are respectively arranged at the two sides of the spinous processes of the human physiological vertebrae 1. The artificial vertebral main body 10 is configured to implanting and replacing an excised or missed host vertebra segment so as to restore and rebuild a physiological height of a spine, and in future, to form a bone fusion with the upper and lower adjacent human physiological vertebrae 1. It may be seen from FIG. 1 that the above artificial vertebral main body 10 and the longitudinal connecting rods 20 are respectively arranged at two sides of a spine cord 2. The artificial vertebral main body 10 and the longitudinal connecting rods 20 are connected via the transverse connecting screws 30. The transverse connecting screws 30 are provided with rod connecting sections corresponding to the longitudinal connecting rods 20. Each of the rod connecting sections includes a through-hole structure, the through-hole structures may accommodate the longitudinal connecting rods 20 to penetrate through it and by locking devices, a position relationship between the through-hole structures in itself and the longitudinal connecting rods 20 is locked. Preferably, the through-hole structures are of an opened groove structure. In the embodiment, the connecting portions 40 are connected to the artificial vertebral main body 10, and each of the connecting portions 40 is provided with a self-tapping through hole 41. The transverse connecting screws 30 are formed screw structures by self-tapping when being screwed to the self-tapping through holes 41. The thread diameters of the thread structures preferably are 1-10 mm.

By applying the technical solution of the embodiment, the transverse connecting screws 30 are closely matched with the screw structures formed by self-tapping, and the connection is stable. As a result, the transverse connecting screws 30 are connected with the connecting portions 40 stably, and the condition that screw threads are dropped out does not occur. Therefore, the artificial vertebral fixing system of the disclosure has a good stability, and the shift phenomenon in the related technology does not occur. In the embodiment, the connecting portions 40 are made of a plastic, such as a Polyethylene (PE) material.

In other embodiments not shown in Fig., each of the connecting portions is provided with a threaded hole; the connecting portions are made of a metal material; the transverse connecting screws are matched with the threaded holes, thereby implementing stable connection between the transverse connecting screws and the connecting portions.

The artificial vertebral main body 10 is a cylindrical body. A vertebra fusion surface is arranged at upper and lower ends of the artificial vertebral main body 10 respectively. Preferably, a cross section of the cylindrical body of the artificial vertebral main body 10 is of a circular shape, a long circular shape, an annular shape, an oval shape, a fan shape, a polygonal shape, a kidney shape, and a graphic shape combined by the above shapes. Preferably, a micropore structure is provided on each of the vertebra fusion surfaces. The micropore structure is a multi-directional micropore structure including a plurality of interconnected micropores. Preferably, the diameters of the micropores of the micropore structure are 100 µm to 1800 µm.

In the technical solution of the embodiment, the artificial vertebral main body 10 is obtained according to CT data of a patient and therefore it can be perfectly matched with the adjacent human physiological vertebrae 1 in structures, thereby improving the stability of the artificial vertebral fixing system.

After the artificial vertebral fixing system is implanted into a human body, the vertebra fusion surfaces of the artificial vertebral main body 10 of the fixing system are closely attached with end plates of upper and lower adjacent host healthy vertebrae. In future, bone cells will be grown into the micropore structure on the vertebra fusion surfaces, such that the end plates of the vertebrae have the bone fusion with the vertebra fusion surfaces, thereby implementing the long-term stabilization of the artificial vertebral main body. Surface morphological structures of the fusion surfaces are obtained by three-dimensional reconstruction for the CT of the patient and thus the fusion surfaces can be perfectly matched with the adjacent human physiological vertebrae 1 in the structures. After the artificial vertebral main body 10 is implanted into a position of a predetermined segment, the vertebra fusion surfaces will be in good attachment with bone substances on the end plates of the upper and lower adjacent healthy vertebra segments, and its cylindrical surface is positioned within physiological surfaces of the healthy vertebrae. The connecting positions 40 are arranged at places between the two vertebra fusion surfaces. One or more connecting portions 40 may be arranged on the artificial vertebral main body 10 according to a length of the vertebra. The connecting portions 40 may form a firm and tight mechanical connection with the transverse connecting screws 30. The height of the artificial vertebral main body 10 will be designed to increase by taking every 0.5-15 mm as a differential gradient, thereby meeting the personal demand of different patients. Preferably, a reinforcing structure is arranged on a surface of the artificial vertebral main body 10 and/or inside the artificial vertebral main body 10.

Multiple fixing threaded holes, which are inclined and are penetrated through the vertebra fusion surfaces to extend upward or downward, are arranged on the artificial vertebral main body 10. Vertebral fixing screws pass through the fixing holes to connect and fix the artificial vertebral main body 10 with the upper and lower adjacent host vertebrae fragments. Preferably, the diameters of the fixing holes are 2-10 mm. Preferably, screw threads are arranged on inner walls of the fixing holes, and the thread pitches of the screw threads are 0.25-5 mm.

Preferably, a bone grafting hole is formed on the artificial vertebral main body 10. One or more bone grafting holes are provided, and the diameters are 2-30 mm. the multiple bone grafting holes are penetrated through one another or communicate via the micropore structure. The micropore structure is a multi-directional micropore structure including a plurality of interconnected micropores. Preferably, the diameters of the micropores of the micropore structure are 100 µm to 1800 µm. The artificial vertebral main body 10 includes the micropore structure, so it may be ensured that the overall structure is light. To ensure the strength, a solid structure is arranged on a middle portion of the micropore structure respectively.

Preferably, when the symptom allows, the artificial vertebral main body 10 may only be fixed using the vertebral fixing screws, and there is no need to use the transverse connecting screws 30, the pedicle screws 60 and the longitudinal connecting rods 20.

Preferably, in the artificial vertebral fixing system of the embodiment, the components such as the artificial vertebral main body 10, the transverse connecting screws 30, the pedicle screws 60 and the longitudinal connecting rods 20 are made of a medical metal and a medical polymer material. It is proved by clinical experiments for many years that most of these medical materials have a good biological performance.

Figure 2:
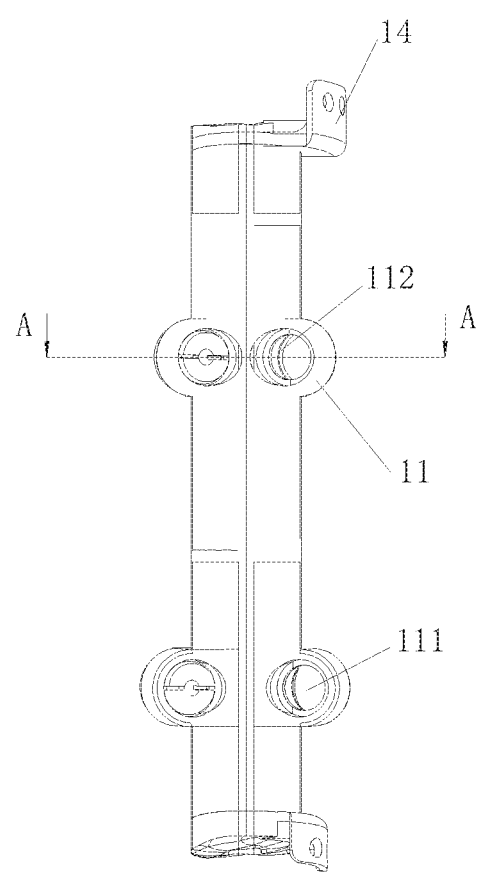
FIG. 2 depicts a structure diagram of an artificial vertebral main body of the artificial vertebral fixing system of FIG. 1.
Figure 4:
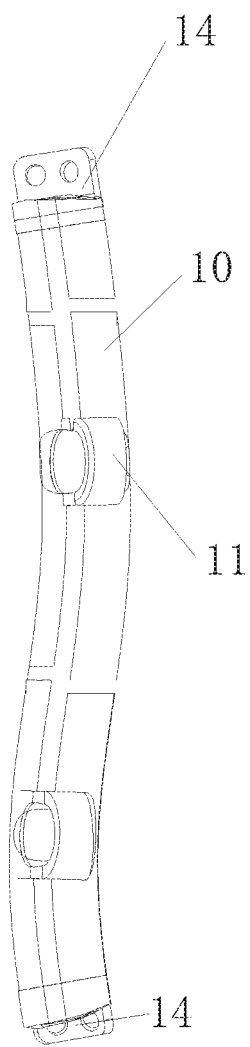
FIG. 4 depicts a structure diagram of the artificial vertebral main body of the artificial vertebral fixing system of FIG. 2.
Figure 5:
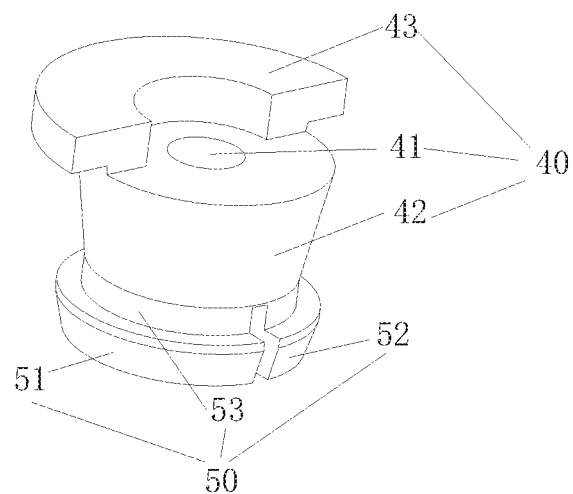
FIG. 5 depicts a structure diagram of a connecting portion of the artificial vertebral fixing system of FIG. 1.
Figure 7:
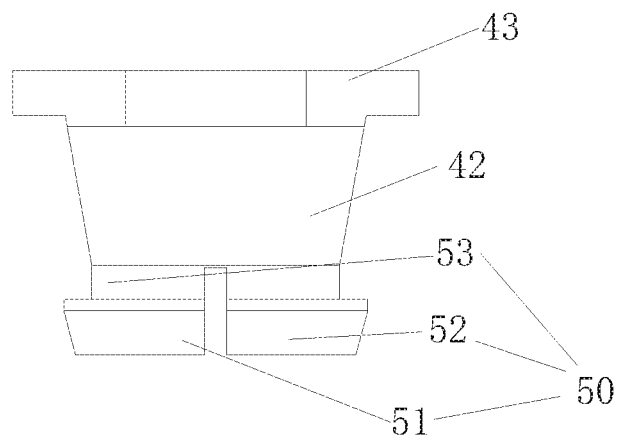
FIG. 7 depicts a front view of the connecting portion of FIG. 5.
Figure 8:
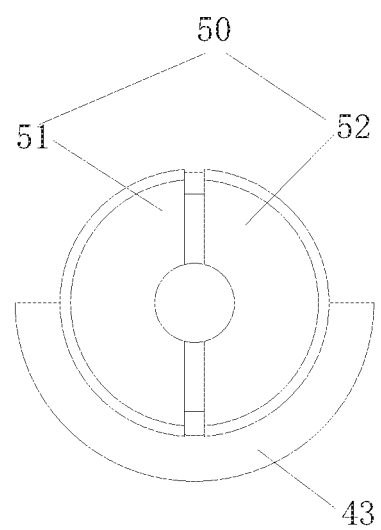
FIG. 8 depicts a bottom view of the connecting portion of FIG. 5.
Figure 9:
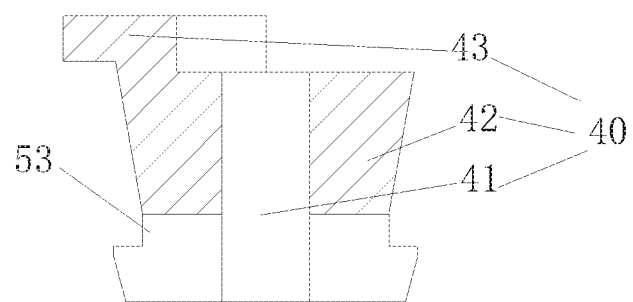
FIG. 9 depicts a sectional view of the connecting portion of FIG. 5.

There are many ways to connect the connecting portions 40 to the artificial vertebral main body 10, for example, to connect or splice via fasteners. In the embodiment, the connecting portions 40 and the artificial vertebral main body 10 are connected together via connecting holes. Specifically, FIG. 2 depicts a structure diagram of an artificial vertebral main body of the artificial vertebral fixing system of FIG. 1, and FIG. 4 depicts a structure diagram of the artificial vertebral main body of the artificial vertebral fixing system of FIG. 1. As shown in FIG. 2 and FIG. 4, in the embodiment, the artificial vertebral main body 10 includes earring structures 11, and the connecting portions 40 on the artificial vertebra are penetrated into the connecting holes 111 of the earring structures 11. By the way of the connecting holes, the quick connection can be implemented between the connecting portions 40 and the artificial vertebral main body 10. In addition, the connecting portions 40 are penetrated into the connecting holes 111 of the earring structures 11, and in the process when the transverse connecting screws 30 are screwed, the connection between the connecting portions 40 and the earring structures 11 will become tighter. And meanwhile, to prevent the connecting portions 40 from rotating in the process when the transverse connecting screws 30 are screwed to the self-tapping through holes 41, as shown in FIG. 5, in the embodiment, each of the connecting portions 40 includes a connecting portion main body 42 and a rotation stopping portion 43 arranged on the connecting portion main body 42. The rotation stopping portions 43 are abutted against and matched with limiting portions 12 of the artificial vertebral main body 10. Preferably, the earring structures 11 are 5-20 mm in the diameters and are made of a plastic. FIG. 5 depicts a structure diagram of a connecting portion and a locking mechanism of the artificial vertebral fixing system of FIG. 1, and FIG. 9 depicts a sectional view of the connecting portion and the locking mechanism of FIG. 5. As shown in FIG. 5 to FIG. 9, in the embodiment, the rotation stopping portions 43 are arc blocks. The arc blocks are easily machined and have a good anti-rotation effect. The limiting portions 12 arranged on the connecting portion main bodies 42 preferably are of a semicircular structure. The arc blocks and the limiting portions 12 may be closely attached, thus improving the stability of the artificial vertebral fixing system.

As shown in FIG. 5, in the embodiment, each of the connecting portions 40 further includes a locking mechanism 50, and the connecting portions 40 are limited in the connecting holes 111 by the ms 50. By virtue of the locking mechanisms 50, it may implement the locking on the connecting portions 40 and the earring structures 11 and prevents the connecting portions 40 from withdrawing from the connecting holes 111.

Figure 6:
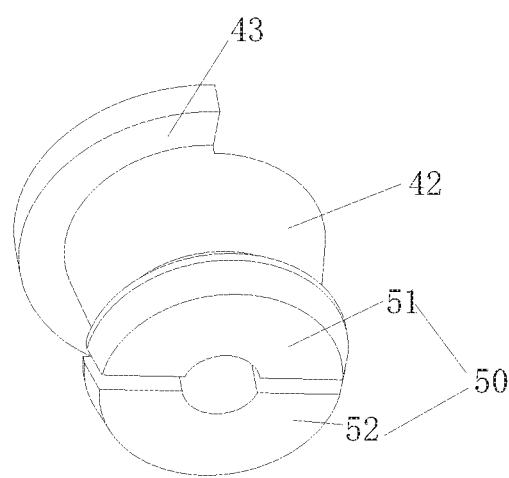
FIG. 6 depicts a structure diagram of another angle of the connecting portion of FIG. 5.

There are many implementation ways for the locking mechanisms 50. In the embodiment, each of the locking mechanisms 50 includes a first fixture block 51 and a second fixture block 52 that are arranged oppositely; the first fixture blocks 51 and the second fixture blocks 52 are protruded from the connecting portion main bodies 42 on radial directions of the connecting portion main bodies 42; a deformation gap is formed between the first fixture blocks 51 and the second fixture blocks 52. Owing to the deformation gaps, the first fixture blocks 51 and the second fixture blocks 52 will be deformed in the process of passing through the connecting holes 111, such that the locking mechanisms 50 pass through the connecting holes 111 conveniently. After the locking mechanisms 50 pass through the connecting holes 111, the first fixture blocks 51 and the second fixture blocks 52 are restored to positions protruded from the connecting portion main bodies 42. In this way, the locking mechanisms 50 can be arranged at certain ends of the connecting holes 111 in a clamping manner and are not withdrawn from the connecting holes 111. As shown in FIG. 6 and FIG. 8, in the embodiment, the deformation gaps are I-shaped openings. Of course, a perform skilled in the art knows that the deformation gaps are not limited to the above structure, as long as there can provide deformation spaces when the first fixture blocks 51 and the second fixture blocks 52 pass through the connecting holes 111.

Each of the locking mechanisms 50 further includes a transitional straight tube section 53; first ends of the transitional straight tube sections 53 are connected with the connecting portion main bodies 42; the first fixture blocks 51 and the second fixture blocks 52 are connected to the transitional straight tube sections 53 and are protruded from the transitional straight tube sections 53 on radial directions of the transitional straight tube sections 53; the transitional straight tube sections 53 are provided with cutting grooves communicating with the deformation gaps. The transitional straight tube sections 53 have two functions, one of which is to guarantee the strength of the connecting portions 40 and prevent the places where the connecting portion main bodies 42 and the locking mechanisms 50 are connected from being weak, and the other is to withdraw a tool conveniently in machining. As shown in FIG. 5 to FIG. 7, in the embodiment, each of the connecting portion main bodies 42 is provided with a first end towards the longitudinal connecting rods 20 and a second end far away from the longitudinal connecting rods 20; the rotation stopping portions 43 are arranged at the first ends of the connecting portion main bodies 42; the locking mechanisms 50 are arranged at the second ends of the connecting portion main bodies 42. When the artificial vertebral main body 10 and the longitudinal connecting rods 20 are connected and matched via the transverse connecting screws 30, because of the above structure, the transverse connecting screws 30 are screwed to the locking mechanisms 50 from the rotation stopping portions 43 of the connecting portion main bodies 42, and in the process of rotation, the connecting portion main bodies 42 and the artificial vertebral main body 10 are matched more closely and are not separated easily.

As shown in FIG. 5 to FIG. 7, in the embodiment, a circumferential outer surface of each of the connecting portion main bodies 42 is of a conical shape; the outer diameters of the connecting portion main bodies 42 are gradually reduced on directions from the first ends to the second ends; the connecting holes 111 of the earring structures 11 are conical holes matched with the connecting portion main bodies 42. The connecting portion main bodies 42 are of the conical shape and need to be connected with the matched conical holes. With the above structure, in the process when the transverse connecting screws 30 are screwed from the first ends of the connecting portion main bodies 42 to the second ends, the connecting portion main bodies 42 and the earring structures 11 are pressed to be tighter and are combined to be closer.

Figure 3:
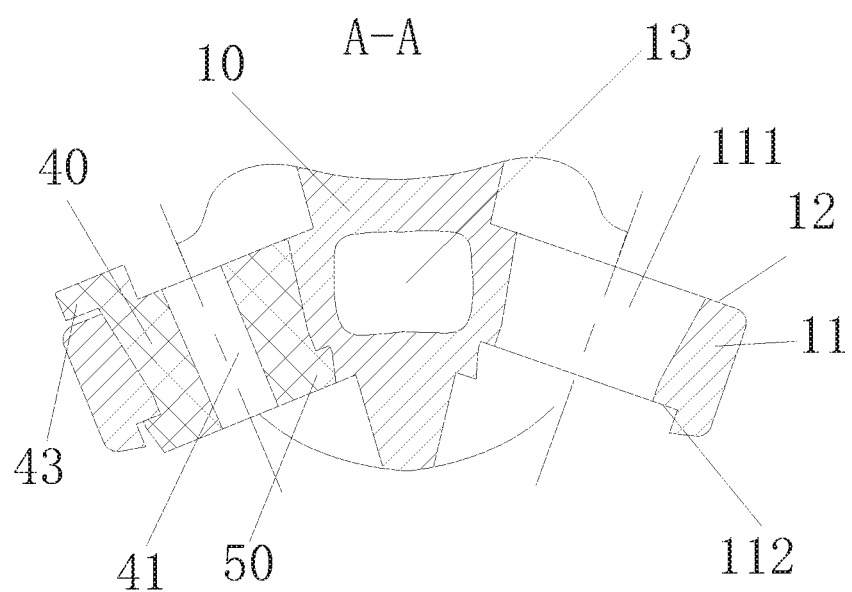
FIG. 3 depicts a sectional view of an A-A direction of the artificial vertebral main body of the artificial vertebral fixing system of FIG. 2.

As shown in FIG. 2 and FIG. 3, in the embodiment, a clamping step 112 is arranged in each of the connecting holes 111 of the earring structures 11; the locking mechanisms 50 are matched with the clamping steps 112. The locking mechanisms 50 are clamped on the clamping steps 112 via the connecting holes 111. The locking mechanisms 50 only are partially protruded from the connecting holes 111. The walls of the connecting holes 111 will take a certain protective effect to the locking mechanisms 50, thereby preventing the locking mechanisms 50 from withdrawing from the connecting holes 111 due to the deformation.

As shown in FIG. 3, in the technical solution of the embodiment, a longitudinal through hole 13 is formed on the artificial vertebral main body 10. The longitudinal through hole 13 may be configured to implant a bone, such that the bone is combined easily.

As shown in FIG. 1, in the embodiment, the artificial vertebral fixing system further includes fixing plates 14 arranged on end portions of the artificial vertebral main body 10; the fixing plates 14 are configured to connect with the human physiological vertebrae 1; fixing holes are formed on the fixing plates 14. The fixing holes preferably are screw holes. In surgery procedures, a doctor will screw the vertebral fixing screws to the end plates of the human upper and lower adjacent host healthy physiological vertebrae 1 via the fixing holes. At this moment, the end plates of the two adjacent host healthy human physiological vertebrae 1 will be closely attached with the vertebra fusion surfaces on the artificial vertebral main body 10 via the vertebrae fixing screws.

As shown in FIG. 1, in the embodiment, the artificial vertebral fixing system further includes pedicle screws 60; the longitudinal connecting rods 20 and the human physiological vertebrae 1 are connected via the pedicle screws 60. By virtue of the above structure, the longitudinal connecting rods 20 can be connected with the adjacent healthy human physiological vertebrae 1 together, and thus, the stability of the artificial vertebral fixing system is effectively improved.

In the embodiment, the pedicle screws 60 and the longitudinal connecting rods 20 will form a fixing and supporting effect for a spine posterior screw-rod system at a posterior side of the spine by a surgery. The transverse connecting screws 30 are configured to connect the artificial vertebral main body 10 and the longitudinal connecting rods 20 one another. The artificial vertebral main body 10 is tightly fixed with the upper and lower adjacent vertebrae via the vertebral fixing screws. And meanwhile, the artificial vertebral main body 10 is further tightly connected and fixed with the spine posterior screw-rod system, formed by the pedicle screws 60 and the longitudinal connecting rods 20, via the transverse connecting screws 30, thereby finally forming the artificial vertebral fixing system. The artificial vertebral fixing system has extremely high anti-rotation and anti-dropping capabilities, and after the surgery, can enable the spine to get the reliable immediate stability, so as to implement the bone fusion between the artificial vertebral main body and the upper and lower adjacent vertebrae as early as possible.

In the technical solution of the embodiment, in order to facilitate the operation of the doctor in the surgery and reduce the types of products and surgical tools, the transverse connecting screws 30 are the same as the pedicle screws 60 in structures.

According to the disclosure, a surgical process of the artificial vertebral fixing system is as follows.

1) A damaged host vertebra fragment to be replaced is taken out.
2) An artificial vertebral main body 10 with an appropriate height is selected and is put into a site where the damaged host vertebra fragment is taken out. When necessary, bone blocks and broken bone particles of an autogenous bone or an allogeneic bone are implanted into a bone grafting hole of the artificial vertebral main body 10, so as to induce crawling growth of bone cells in future.
3) Vertebral fixing screws with appropriate diameter and length are selected and are screwed to end plates of upper and lower adjacent host healthy vertebrae via fixing holes on the artificial vertebral main body. At this moment, the end plates of the two adjacent host healthy vertebrae will be tightly attached to vertebra fusion surfaces on the artificial vertebral main body 10 via the vertebral fixing screws.
4) Pedicle screws 60 and longitudinal connecting rods 20 are placed at a posterior side of the spine, so as to position the adjacent healthy vertebrae.
5) Transverse connecting screws 30 are placed, such that the artificial vertebral main body 10 is connected and positioned with the longitudinal connecting rods 20 at the posterior side of the spine.

From the above description, it may be observed that the embodiment of the disclosure achieves the following technical effects.

1) The cross-segment vertebral customization can be implemented and the fixing is stable.
2) A physiological curved of the spine is customized by following an arc design and according to characteristics of a normal person.
3) The artificial vertebral main body and the posterior screw-rod system are firmly connected via the pedicle screws to form an integral truss structure.
4) The posterior screw-rod system is adaptive to the pedicle screws of any manufacturer, so the use is flexible.
5) In cooperation with bionic shapes of the reserved upper and lower vertebra contact surfaces, it is beneficial to supporting effectively.
6) The fixing plates are provided at upper and lower ends of the customized artificial vertebral main body and are connected with the reserved upper and lower vertebrae by multiple screws, so the auxiliary fixing is implemented.
7) For the artificial vertebral main body, a reinforcing rib structure is provided inside so as to guarantee the enough strength.
8) To customize the upper and lower ends of the artificial vertebral main body, the porous structures into which bones are grown are provided.
9) The connecting portions are locked flexibly, the installation effect is good and the fixing is stable.

The above are a preferable embodiment of the disclosure and are not intended to limit the disclosure. Those of ordinary skill in the art may make various alternations and improvements to the disclosure. Any modification, equivalent replacement and improvement made within the spirit and the principle of the disclosure shall also fall within the scope of protection of the disclosure.

What is claimed is:
1. An artificial vertebra fixing system, comprising:
an artificial vertebra main body adapted to be arranged between adjacent human physiological vertebrae;
two longitudinal connecting rods respectively adapted to be arranged at two sides of spinous processes of the human physiological vertebrae;
transverse connecting screws, connected between the artificial vertebra main body and each of the longitudinal connecting rods, respectively; and
a connecting portion connected to the artificial vertebra main body, the connecting portion being provided with a self-tapping through hole or a threaded hole, wherein
when the connecting portion is provided with the self-tapping through hole, a corresponding one of the transverse connecting screws is formed into a thread structure by self-tapping when screwed to the self-tapping through hole, and
when the connecting portion is provided with the threaded hole, a corresponding one of the transverse connecting screws includes threading matched with the threaded hole, and further wherein
the artificial vertebra main body comprises an earring structure;
the connecting portion is penetrated into a connecting hole of the earring structure;
the connecting portion comprises a connecting portion main body and a rotation stopping portion arranged on the connecting portion main body;
the rotation stopping portion is abutted against and matched with a limiting portion of the artificial vertebra main body;
the rotation stopping portion is an arc block;
the limiting portion is arranged on the connecting portion main body is of a semicircular structure;
the arc block and the limiting portion are closely attached;
the connecting portion further comprises a locking mechanism;
the connecting portion is limited in the connecting hole by the locking mechanism;
a clamping step is arranged in the connecting hole of the earring structure;
the locking mechanism is matched with the clamping step;
the locking mechanism comprises a first fixture block and a second fixture block that are arranged oppositely;
the first fixture block and the second fixture block protrude from the connecting portion main body in a radial direction from the connecting portion main body; and
a deformation gap is formed between the first fixture block and the second fixture block.
2. The artificial vertebra fixing system as claimed in claim 1, wherein
the connecting portion main body is provided with a first end towards the longitudinal connecting rods and a second end far away from the longitudinal connecting rods;

the rotation stopping portion is arranged at the first end of the connecting portion main body; and the locking mechanism is arranged at the second end of the connecting portion main body.

3. The artificial vertebra fixing system as claimed in claim 1, wherein the locking mechanism further comprises a transitional straight tube section;

a first end of the transitional straight tube section is connected with the connecting portion main body;

the first fixture block and the second fixture block are connected to the transitional straight tube section and protrude from the transitional straight tube section in a radial direction from the transitional straight tube section; and the transitional straight tube section is provided with a cutting groove communicating with the deformation gap.

4. The artificial vertebra fixing system as claimed in claim 1, wherein a circumferential outer surface of the connecting portion main body is of a conical shape;

an outer diameter of the connecting portion main body is gradually reduced on a direction from the rotation stopping portion to the locking mechanism; and the connecting hole of the earring structure is a conical hole matched with the connecting portion main body.

5. The artificial vertebra fixing system as claimed in claim 1, wherein a longitudinal through hole is formed on the artificial vertebra main body.

6. The artificial vertebra fixing system as claimed in claim 1, wherein the artificial vertebra fixing system further comprises fixing plates arranged on end portions of the artificial vertebra main body;

the fixing plates are configured to connect with the human physiological vertebrae; and a fixing hole is formed on each of the fixing plates.

7. The artificial vertebra fixing system as claimed in claim 1, wherein the artificial vertebra fixing system further comprises pedicle screws; and the longitudinal connecting rods are configured to be connected to the human physiological vertebrae via the pedicle screws.

8. The artificial vertebra fixing system as claimed in claim 7, wherein the transverse connecting screws are the same as each of the pedicle screws in structure.

9. The artificial vertebra fixing system as claimed in claim 1, wherein the artificial vertebra main body is designed according to Computed Tomography data of a patient.

* * * * *